United States Patent [19]
Meryman

[11] Patent Number: 5,601,972
[45] Date of Patent: Feb. 11, 1997

[54] LONG TERM STORAGE OF RED CELLS IN UNFROZEN SOLUTION

[75] Inventor: Harold R. Meryman, Ashton, Md.

[73] Assignee: Organ, Inc., Chicago, Ill.

[21] Appl. No.: 409,599

[22] Filed: Mar. 24, 1995

[51] Int. Cl.$^6$ .................... A01N 1/02; A61K 35/14; A61K 35/18
[52] U.S. Cl. ................. 435/2; 424/529; 424/533
[58] Field of Search ............... 435/2; 424/529, 424/533

[56] References Cited

U.S. PATENT DOCUMENTS

| | | | |
|---|---|---|---|
| 4,061,537 | 12/1977 | Seiler et al. | 195/1.7 |
| 4,585,735 | 4/1986 | Meryman et al. | 435/2 |
| 5,250,303 | 10/1993 | Meryman et al. | 424/533 |

OTHER PUBLICATIONS

Law, P., Cryopreservation of Platelets: Current Status, Plasma Ther Transfus Technol 1982 3: 317–326.
H. T. Meryman, "Influence of certain neutral solutes on red cell membrane area and permeability during hypotonic stress," American Journal of Physiology, vol.225, No.2, Aug. 1973.

*Primary Examiner*—Ralph Gitomer
*Attorney, Agent, or Firm*—Oliff & Berridge

[57] ABSTRACT

A method for prolonging storage shelf-life of red blood cells under refrigerated conditions includes separating plasma from the red blood cells while retaining residual plasma and adding a biologically compatible solution having an effective osmolality of less than 70 mOsm to the red blood cells. The biologically compatible solution preferably includes at least one penetrating solute that penetrates red cells more slowly than water and substantially no non-penetrating anions and non-penetrating non-electrolytes.

20 Claims, 1 Drawing Sheet

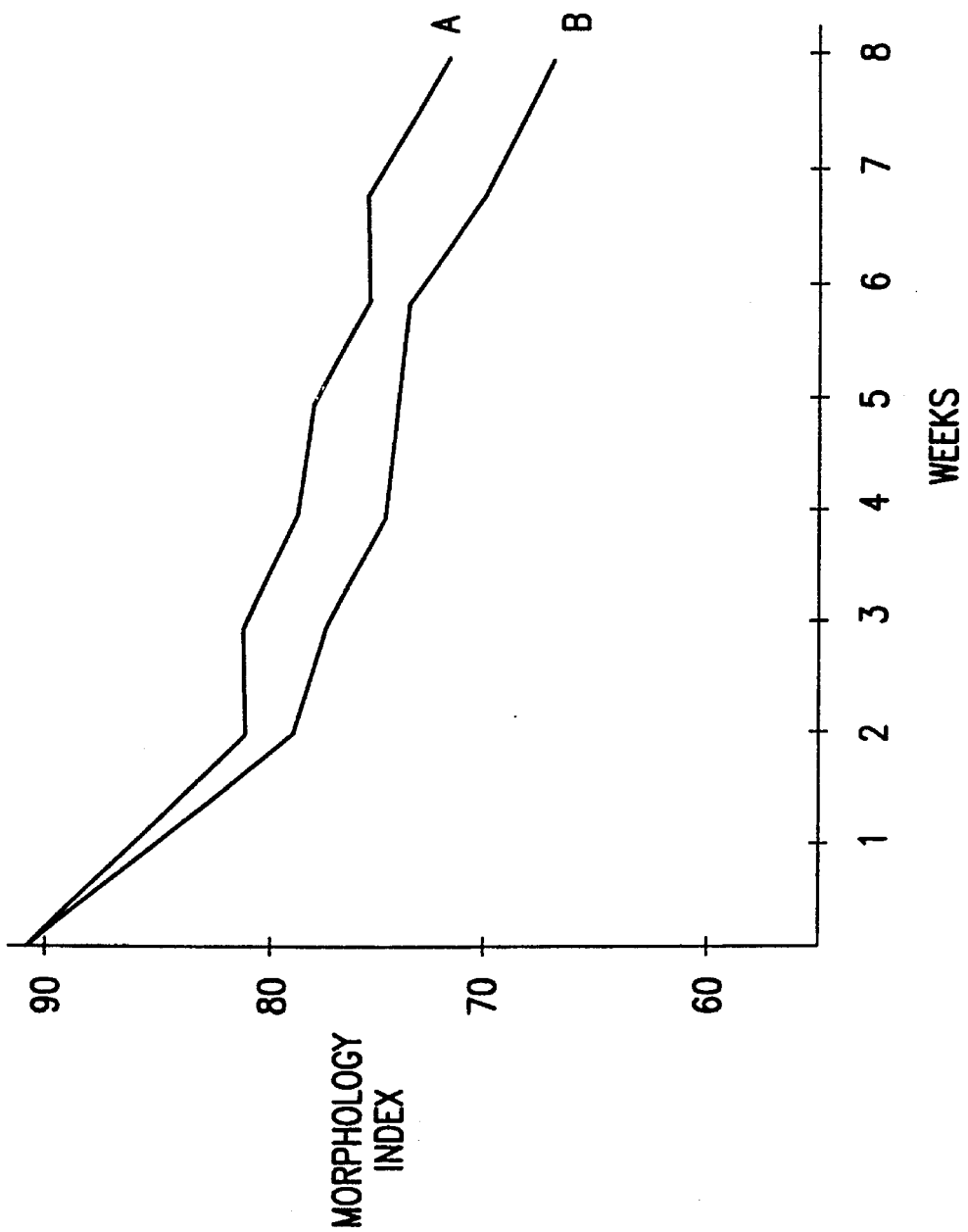

LONG TERM STORAGE OF RED CELLS IN UNFROZEN SOLUTION

BACKGROUND OF THE INVENTION

This invention relates to a method for long-term refrigerated storage of red cells.

Red cells stored by refrigeration have a limited shelf-life depending on the solutions in which they are stored. Shelf-life is determined, in the United States at least, by measurements of the proportion of cells circulating in the recipient 24-hrs after transfusion. The FDA has unofficially established 75% as the minimum for a licensed product. The quantity of free hemoglobin that is transfused can also limit shelf-life. Although no official maximum has been established, there is general agreement that hemolysis should not exceed 1%.

The two general methods for the refrigerated storage of human red blood cells are: (1) refrigerated storage in the original anticoagulant solution; and (2) refrigerated storage after separation of the red cells from the original anticoagulant solution, and resuspension of the cells in a solution that is specifically designed for red cell storage. When either of these methods is used, at least a residual amount of plasma remains in the red cell solution.

For storage in the original anticoagulant, whole blood is conventionally drawn into a solution containing citrate, phosphate, dextrose (d-glucose) and adenine (CPDA-1). The blood is centrifuged at about 1500×G (soft spin) and the plasma is removed, leaving a red cell suspension with a hematocrit of about 75%. Platelets can be removed from the plasma by a second sedimentation. Cells collected in CPDA-1 can be stored for 5 weeks without further treatment with or without removal of the plasma.

For resuspension of the red cells and storage in a preservation solution, blood is conventionally drawn into a solution containing only citrate, phosphate and glucose. The blood is centrifuged at about the same speed as described above but the red cells are then resuspended in approximately 100 ml of an additive solution, resulting in a red cell suspension at a hematocrit of approximately 5%. The two currently-licensed additive solutions in the United States are Adsol and Nutricel, as defined in Table 1. Another known additive solution, Sagman, has not been licensed in the United States. Cells stored with these additive solutions have a six-week shelf-life.

TABLE 1

| Ingredient | CPDA-1 (mM) | ADSOL (mM) | NUTRICEL (mM) |
|---|---|---|---|
| NaCitrate | 89.6 | — | 20.0 |
| cit. acid | 15.6 | — | 2.0 |
| dextrose | 161.0 | 111.0 | 55.5 |
| $NaH_2PO_4$ | 16.1 | — | 20.0 |
| Adenine | 2.0 | 2.0 | 2.2 |
| Mannitol | — | 41.2 | — |
| NaCl | — | 154.0 | 70.1 |
| Osmolality (mOsm) | 323 | 342 | 244 |
| pH | 5.7 | 5.5 | 5.8 |

CPDA-1 and ADSOL are sold by Baxter Travenol and NUTRICEL is sold by Cutter. Osmolality is the effective osmolality contributed by the non-penetrating constituents.

During storage, human red blood cells undergo morphological and biochemical changes, including decreases in the cellular level of adenosine triphosphate (ATP) and 2,3-diphosphoglycerate (2,3-DPG), changes in cellular morphology, and progressive hemolysis. The concentration of ATP, after a brief initial rise, progressively declines to between 30 and 40% of its initial level after six weeks of storage. The fluidity of the cell membrane of red cells, which is essential for the passage of red cells through the narrow channels in the spleen and liver, is loosely correlated with the level of ATP.

The primary function of red cells in the circulation is to deliver oxygen to the tissues. A unique characteristic of hemoglobin is that it can unload much of its oxygen even though the partial pressure of oxygen in the tissues may be relatively high. A compound called 2,3-diphosphoglycerate (2,3-DPG) is essential to this process and, in its absence, oxygen is not efficiently delivered to the tissues. During refrigerated storage as currently practiced, the level of 2,3-DPG falls rapidly after about three or four days of storage and approaches zero by about ten days.

Morphological changes occur during storage, ultimately leading to the development of spicules on the red cells (echinocytosis). These spicules can bud off as vesicles, radically changing the surface-to-volume ratio of the cells and their ability to deform on passing through narrow channels. Such cells will be filtered out of the circulation by the spleen and liver following transfusion. As stated above, to be acceptable for transfusion at least 75% of the red cells that are transfused must be capable of remaining in circulation twenty-four hours following the transfusion. The concentration of ATP and the morphology of red cells serve as indicators of the suitability of stored cells for transfusion.

In order to prolong the shelf-life of transfusable red blood cells, it is necessary to store the cells or treat them in some manner that prevents a rapid decline in ATP and, if possible, 2,3-DPG. Solutions that prolong the shelf-life of red cells are known (see, e.g., Meryman, U.S. Pat. No. 4,585,735, and Meryman, U.S. Pat. No. 5,250,303, both of which are herein incorporated in their entirety by reference). Typically such solutions contain citrate, phosphate, glucose and adenine and occasionally other ingredients that function to prolong shelf-life by maintaining the level of ATP in the cells. It is known to use an additive solution having an effective osmolality as low as 121 mOsm. However, solutions with lower effective osmolalities are not used. In addition, glycolytic activity is enhanced in red blood cells if the intracellular pH (hereinafter $ph_i$) measured at 4° C. is about 7.4.

The effective osmolality of the suspending solution is another factor of importance in extending red cell storage time. It has been shown that effective hypotonicity substantially reduces hemolysis and improves red cell morphology during storage. Although the mechanism has not been proven, it is probable that osmotic swelling increases cell surface tension, thereby facilitating the shape changes usually associated with stored red cells.

When red cells are washed, it is possible to achieve the maximum hypotonicity just short of hemolysis from cell swelling. However, washing red cell units is expensive and not currently justified by the extended shelf-life obtained. The standard procedure currently in use involves the removal of plasma following an initial sedimentation and the addition of 100 ml of an additive solution to approximately 200 ml of red cells and 50 ml of residual plasma.

The hypotonicity of the additive solution is limited by the danger of hemolysis during the addition of the solution. Although, theoretically, it is not necessary for the additive solution to contain enough solute to osmotically support the red cells since the plasma provides additional osmotic support, at the time of adding the solution, before mixing has occurred, some red cells will come into contact with the additive solution. If the additive solution is too hypotonic, these red cells will burst (hemolyze). As a result, solutions that are too hypotonic cannot be used. Therefore, the final osmolality of the solution after mixing with the cells and the residual plasma is not particularly hypotonic and the advantages of hypotonicity are insufficient.

Red cells, which are normally bi-concave disks, can swell to nearly twice their normal volume at an external osmolality of approximately 170 mOsm before they hemolyze. However, it has also shown that when solutes from the left end of the Hofmeister series, the so-called macromolecular stabilizers, are present both inside and outside the cell, a membrane expansion takes place and red cells can swell beyond their normal hemolytic volume and do not begin to hemolyze until the extracellular osmolality is approximately 70 mOsm. Meryman, H.T., "Influence of certain neutral solutes on red cell membrane area and permeability during hypotonic stress," Am. Journ. of Physiol., 225:365–371, 1973.

Because of the critical need for transfusable red blood cells, it is of great importance not only to develop methods and solutions that not only maintain high intracellular levels of both ATP and 2,3-DPG, good morphology and low hemolysis after washing, but also to develop methods for the routine collection and resuspension of unwashed red cells with better storage characteristics than are achieved by current procedures.

SUMMARY OF THE INVENTION

The invention provides a method for storing red blood cells that leads to a greater degree of hypotonicity during storage without increasing the risk of cell hemolysis during the addition of storage solution to the red cells.

This invention provides a method for prolonging storage shelf-life of red blood cells under refrigerated conditions, comprising: separating plasma from the red blood cells while retaining residual plasma; and adding a biologically compatible solution to said red blood cells, wherein said biologically compatible solution has an effective osmolality of less than 70 mOsm.

This invention also provides a method for prolonging storage shelf-life of red blood cells under refrigerated conditions, wherein the biologically compatible solution added to the red blood cells comprises at least one penetrating solute that penetrates red blood cells more slowly than water and substantially no non-penetrating anions and non-penetrating non-electrolytes.

BRIEF DESCRIPTION OF THE DRAWING

FIG. 1 depicts the morphological index of red cells during eight weeks of storage for an embodiment of the present invention and a comparative embodiment.

DETAILED DESCRIPTION OF PREFERRED EMBODIMENTS

Unless defined otherwise, all technical and scientific terms used herein have the same meaning as is commonly understood by one of ordinary skill in the art. All publications mentioned herein are incorporated by reference.

As used herein, "prolonging storage shelf-life" refers to preserving viable red blood cells for an extended period of time with low hemolysis and with cell morphological index and levels of ATP and 2,3-DPG that are greater than the levels of morphological index, ATP and 2,3-DPG in cells stored by the conventional methods known to those of skill in the art.

As used herein, a "biologically compatible solution" is a transfusable solution in which cells that are contacted therewith retain viability. Contacting includes any process in which the cells are in some manner exposed to the solution and includes, but is not limited to, suspension of the cells in the solution. A biologically compatible solution has a pH and a salt concentration that are suitable for maintaining the integrity of the cell membrane and do not inhibit or destroy the biological and physiological reactions of the cells contacted therewith. Typically a biologically compatible solution has a pH between 6 and 9.5 and is isotonic or only moderately hypotonic or hypertonic.

As used herein, a "penetrating solute" is a solute that is capable of freely traversing the cell membrane of red blood cells. Such a solute may be either a small non-electrolyte such as glucose, or it may be a small anion such as chloride, acetate or phosphate. "Non-penetrating solutes" include larger non-electrolytes such as mannitol and sucrose, or large anions such as citrate, glycolate, and glycerophosphate. Cations, because of their charge, will not penetrate the cell membranes. An exception is the ammonium ion that enters the cell as the neutral molecule, ammonia, and reestablishes the ionized state inside the cell.

As used herein, a "slowly penetrating solute" is a penetrating solute that is capable of freely traversing the cell membrane of red blood cells, but which does so at a rate slower than water. The slowly penetrating solute must penetrate slowly enough such that the additive solution mixes sufficiently with the plasma before the osmotic support provided by the slowly penetrating solute is lost by its diffusion into the cell. Thus, if the extracellular solution is aggressively mixed, the rate of diffusion of the slowly penetrating solute may be increased. In general, the slowly penetrating solute should not reach equilibrium across the cell membrane in less than one second. Preferably, the slowly penetrating solute does not reach equilibrium in less than 10 seconds; more preferably in less than 30 seconds; and even more preferably in less than one minute. Such a solute may include, but is not limited to, solutes such as glucose, glycerol and D-xylose.

As used herein, "residual plasma" refers to the amount of the plasma that remains in a red cell suspension after the plasma is separated from the red cells through centrifugation and a plasma press as conventionally practiced by one of ordinary skill in the art. Generally, about 50 ml of residual plasma remain in a red cell suspension of 260 ml.

As used herein, "effective osmolality" refers to the combined osmolality of solutes that do not penetrate the red cell membrane and therefore serve to determine the volume of the red cell.

As used herein, "refrigerated conditions" refers to conditions for storing red blood cells under refrigeration. Refrigerated conditions include, but are not limited to, temperatures of 4°±2° C.

It has been discovered that the hypotonicity of the additive solution can be increased by using an additive solution comprising a penetrating solute that penetrates the red blood cells more slowly than water. In particular, a biologically compatible solution having an effective osmolality of less than 70 mOsm can be used. An aqueous solution having these properties can be formed, for example, by controlling an amount of non-penetrating solutes in the solution such that the osmolality of the solution is less than 70 mOsm. Then, the solution can be brought to a level isotonic or nearly isotonic with the red cell suspension by increasing the osmolality of the solution using a slowly penetrating solute. The resulting solution provides the necessary osmotic support to avoid substantial hemolysis at the time of the addition of the solution to the cell suspension.

A slowly penetrating solute enters red cells relatively slowly but it will ultimately approach concentration equilibrium across the cell membrane. This means that, for example, red cells can be mixed with an isotonic solution of glucose in water without hemolysis. The osmotic support of the extracellular glucose would be equal to that of the intracellular hemoglobin and salts. Therefore, there would be no change in red cell volume.

However, as the glucose progressively enters the cells, the osmotic support by the glucose is progressively lost and the cells will swell. In terms of its osmotic effect, the end result would be as though pure water had been added to the cell suspension and the cells will swell in response to the diminishing osmolality of the extracellular solution. If there were no non-penetrating solutes in the extracellular solution, water would continually enter the cells until they hemolyze. But, in this invention, even if the additive solution contains no non-penetrating solutes, the residual plasma provides sufficient extracellular osmotic support to avoid hemolysis once equilibration has occurred.

Once the addition of solution is complete, the red cells do not require as much osmotic support. Water enters the red cells, diluting the non-penetrating solutes therein. This decreases the intracellular osmolality of the red cells, thereby decreasing the required extracellular osmolality. At the same time, the osmotic movement of water into the red cells will result in some concentration of the dilute extracellular plasma. Therefore, as the water enters the cells the non-penetrating solutes of the plasma, particularly sodium, provide increased osmotic support. The extent to which the storage solution dilutes the residual plasma will determine the hemolytic volume so that, in practice, the minimum effective osmolality of the final storage solution that will not cause hemolysis will fall somewhere between 300 and 70 mOsm and may be determined by routine experimentation.

Because the additive solution comprises at least one solute that penetrates the cells more slowly than water, this equilibration is able to occur before a solution that does not osmotically support the red cells comes into contact with the red cells. In the end, there is osmotic equilibration between those intracellular solutes that do not freely diffuse out of the cells, predominantly hemoglobin and potassium, and those extracellular solutes that do not penetrate the cell, predominantly the sodium in the plasma. The net result will be an increase in cell volume. This cell swelling provides the benefits of hypotonicity during storage.

Because the residual plasma provides sufficient extracellular osmotic support, the effective osmolality of the additive solution may be less than 70 mOsm. Preferably the effective osmolality of the biologically compatible solution is less than 60 mOsm; more preferably, the effective osmolality of the solution is less than 50 mOsm; even more preferably the effective osmolality is less than 25 mOsm; even more preferably the effective osmolality is less than 15 mOsm; and even more preferably the effective osmolality is less than 5 mOsm. In fact, in the most preferred embodiment of this invention, the effective osmolality of the biologically compatible solution is zero. In this embodiment, the entire extracellular support is provided by the non-penetrating solutes of the residual plasma after penetration of the cell by the slowly penetrating solute.

The biologically compatible solution is preferably buffered. In addition, preferably, the pH of the solution is higher than the pH of the red cell suspension. Further, the additive solution is preferably hypotonic to the red cells, although it could alternatively be isotonic or hypertonic to the red cells. Once the slowly penetrating solute penetrates the red cells, the additive solution per se is hypotonic to the red cells.

The biologically compatible solution may also contain adenine, preferably in only a small amount, for example, two mmol. Further, the additive solution may contain phosphate, for example, in the form of sodium phosphate, but again preferably only a small amount. In addition, preferably, the solution contains substantially no non-penetrating anions and non-penetrating non-electrolytes.

Glucose is a preferred slowly penetrating solute for several reasons. First, glucose is necessary to support red cell glycolysis. Secondly, it is a familiar agent for transfusion. Finally, it is a macromolecular stabilizer.

A major goal of this invention is to maximize the volume of the red cells during storage in order to gain full advantage of the benefits of volume increase which improves cell morphology and reduces hemolysis during storage. Since the constituents of a preferred embodiment of this invention, namely, a solution comprising glucose, phosphate and adenine, are all macromolecular stabilizers, this solution can reduce the osmolality at which red cells will reach hemolytic volume through membrane expansion.

For example, 100 ml of isotonic glucose can be combined with the cell suspension containing approximately 200 ml of red cells and 50 ml of residual plasma. The glucose provides transient osmotic support to prevent hemolysis during mixing but then equilibrates across the cell membrane so that its "effective" osmolality is 0. As glucose equilibrates across the cell membrane, it no longer provides osmotic support for the cell and it is as if 100 ml of water had been added to the cell suspension. Because of the diminishing osmolality of the extracellular solution, the red cells swell. The net result would be an increase in cell volume of approximately 30%. In this example, the effective osmolality of the cell suspension after mixture with the plasma and equilibration of the glucose will be approximately 200 mOsm. This is substantially more than necessary to prevent hemolysis even in the absence of membrane expansion.

If a larger volume of additive solution were to be used, more cell swelling could be achieved. The larger dilution would both reduce the final effective osmolality and increase the proportion of stabilizer solutes, thereby enhancing the membrane expansion, and permitting the effective osmolality of the final solution to fall below 170 mOsm without hemolysis.

One skilled in the art will recognize that the method discussed above may be adjusted as necessary to achieve a storage solution with specific characteristics. The invention will now be further described with reference to a specific embodiment thereof, it being understood that the example is intended to be illustrative only, and the invention is not intended to be limited to the materials, conditions, process parameters, etc. recited therein.

Example 1

A red cell suspension is obtained by drawing blood into a solution containing citrate, phosphate and glucose. The blood is centrifuged at about 1500×G and the plasma is removed. 100 ml of additive solution A, as defined in Table 2, is added to the red cell suspension and the resultant solution is stored at 4° C. for eight weeks. The morphology index of the red cells during refrigerated storage is demonstrated in FIG. 1.

Comparative Example 1

A red cell suspension is obtained as above. 100 ml of additive solution B, as defined in Table 2, is added to the red cell suspension and the resultant solution is stored at 4° C. for eight weeks. The morphology index of the red cells during refrigerated storage is demonstrated in FIG. 1.

TABLE 2

| Ingredient | A (mM) | B (mM) |
|---|---|---|
| Glucose | 139 | 69 |
| NaCitrate | — | 18.4 |
| $Na_2HPO_4$ | 12 | 12 |
| $NaH_2PO_4$ | 2.9 | 2.9 |
| Adenine | 2 | 2 |
| Mannitol | — | 22 |
| Osmolality (mOsm) | | |
| Total | 176 | 176 |
| Effective | 34 | 109 |
| pH | 7.5 | 7.5 |

The morphology index of red cells stored according to Example 1 is maintained at acceptable levels for a longer period of time without any statistically significant change in the amount of red cell hemolysis. In particular, the red cell morphology of red cells stored according to Example 1 has an average 5% improvement over the red cell morphology of red cells stored according to Comparative Example 1. Further, the morphology index decreases to approximately 75% in six weeks for red cells stored according to Comparative Example 1; whereas, in Example 1, the morphology index does not decrease to 75% until eight weeks of refrigerated storage. Thus, the red cells can be stored for a longer period of time using additive solutions according to the present invention.

What is claimed is:

1. A method for preparing red cells for storage under refrigerated conditions, comprising:
   separating plasma from the red cells in a red cell suspension while retaining residual plasma; and
   adding a biologically compatible solution to said red cells, wherein said biologically compatible solution has an effective osmolality of less than 70 mOsm.

2. The method of claim 1, wherein said biologically compatible solution comprises at least one penetrating solute that penetrates red cell membranes more slowly than water.

3. The method of claim 2, wherein said penetrating solute is glucose.

4. The method of claim 1, wherein said biologically compatible solution has an effective osmolality of less than 60 mOsm.

5. The method of claim 1, wherein said biologically compatible solution has an effective osmolality of less than 50 mOsm.

6. The method of claim 1, wherein said biologically compatible solution has an effective osmolality of less than 25 mOsm.

7. The method of claim 1, wherein said biologically compatible solution has an effective osmolality of less than 15 mOsm.

8. The method of claim 1, wherein said biologically compatible solution has an effective osmolality of less than 5 mOsm.

9. The method of claim 1, wherein said biologically compatible solution has an effective osmolality of zero.

10. The method of claim 1, wherein the biologically compatible solution comprises at least one member selected from the group consisting of adenine and phosphate.

11. The method of claim 10, wherein the biologically compatible solution comprises glucose, adenine, and phosphate.

12. The method of claim 1, wherein the plasma is separated from the red cells by centrifugation.

13. The method of claim 1, wherein the biologically compatible solution is hypotonic to the red cells.

14. The method of claim 1, wherein the pH of the biologically compatible solution is greater than the pH of the red cell suspension.

15. A method for preparing of red cells for storage under refrigerated conditions, comprising:
    separating plasma from the red cells in a red cell suspension while retaining residual plasma; and
    adding a biologically compatible solution to said red cells, wherein said biologically compatible solution comprises at least one penetrating solute that penetrates red cell membrane more slowly than water and substantially no non-penetrating anions or non-penetrating non-electrolytes.

16. The method of claim 15, wherein the biologically compatible solution is hypotonic to the red cells.

17. The method of claim 15, wherein the pH of the biologically compatible solution is greater than the pH of the red cell suspension.

18. The method of claim 15, wherein said biologically compatible solution contains no non-penetrating solutes.

19. The method of claim 15, wherein the slowly penetrating solute is glucose.

20. The method of claim 2, wherein said penetrating solute does not reach equilibrium across the red cell membranes in less than one second.

* * * * *